(12) United States Patent
Grøndahl

(10) Patent No.: US 6,544,166 B1
(45) Date of Patent: Apr. 8, 2003

(54) TREATMENT OF HUMAN INFERTILITY

(76) Inventor: Christian Grøndahl, Irisvej 19, Dk-3500 Vaerlose (DK)

(*) Notice: Subject to any disclaimer, the term of this patent is extended or adjusted under 35 U.S.C. 154(b) by 0 days.

(21) Appl. No.: 09/718,710

(22) Filed: Nov. 22, 2000

Related U.S. Application Data
(60) Provisional application No. 60/241,806, filed on Oct. 18, 2000.

(30) Foreign Application Priority Data

Nov. 25, 1999 (DK) .......................................... 1999 01705

(51) Int. Cl.⁷ .............................................. A61D 19/00
(52) U.S. Cl. ........................................................ 600/33
(58) Field of Search ...................... 600/33–35; 128/898; 435/366, 363

(56) References Cited

FOREIGN PATENT DOCUMENTS

| CA | 2199663 | 3/1997 |
|---|---|---|
| WO | WO 99/61010 | 2/1999 |

OTHER PUBLICATIONS

A.A. Fouladi Nashta, et al., "Maintenance of Bovine Oocytes in Meiotic Arrest and Subsequent Development in Vitro: A Comparative Evaluation of Antral Follicle Culture with Other Methods" Biology of Reproduction vol. 59, pp. 255–262b (1998).

Ottesen, Jan H., "The Effect Of Meiosis Activating Sterol (MAS) and Some Oxysterols on the Resumption of Meiosis in Mouse Oocytes Cultered In Vitro" Biology of Reproduction vol. 56, Part 57 p. 97 (1997).

Stephen M. Downs, et al., "Hypexanthine is the Principle Inhibitor of Murine Oocyte Maturation in a Low Molecular Weight Fraction of Porcine Follicular Fluid" Proc. Natl. Acad. Sci, USA., Developmental Biology., vol. 82, pp. 454–458 (1985).

John J. Eppig et al., Developmental Biology, The Effect of Hypoxanthine on Mouse Oocyte Growth and Development in Vitro: Maintenance of Meiotic Arrest and Gonadotropin–Induced Oocyte Maturation, vol. 119., pp. 313–321 (1986).

Stephen M. Downs "Purine Control of Mouse Oocyte Maturation: Evidence That Nonmetabolized Hypoxanthine Maintains Meiotic Arrest" Molecular Reproduction and Development, vol. 35., pp. 82–94 (1993).

John J. Eppig et al., "Hypoxanthine and Adenosine in Murine Ovarian Follicular Fluid:Concentrations and Activity in Maintaining Oocyte Meiotic Arrest" Biology of Reproduction, vol. 33., pp. 1041–1049 (1985).

Stephen M. Downs et al., "Developmental Capacity of Mouse Oocytes following maintenance of Meiotic Arrest in Vitro" Gamete Research, vol. 15, pp. 305–316 (1986).

K.Y. Cha et al., "Viability of Human Follicular Oocytes Collected from Unstimulated Ovaries and Matured and Fertilized in vitro" Reproductive Fertility Development, vol. 4., pp. 695–701 (1992).

Stephen M. Downs et al., "Differential Regulation of Oocyte Maturation And Cumulus Expansion in the Mouse Oocyte–Cumulus Cell Complex by Site–Selective Analogs of Cyclic Adenosine Monophosphate", vol. 172., p. 72–85 (1995).

A. Tsafriri et al., "Oocyte Maturation Involves Compartmentalization And Opposing Changes of camp Levels in Follicular Somatic and Germ Cells: Studies Using Selective Phosphodiesterase Inhibitors", Developmental Biology, vol. 178., pp. 393–402 (1996).

Anne Grete Byskov et al., "Induction of Meiosis in Fetal Mouse Testis In Vitro" Developmental Biology, vol. 52., pp. 193–200 (1976).

E. Knobil et al., "Embryology of Mammalian Gonads and Ducts", The Physiology of Reproduction, pp. 487–540 (1994).

Anne Grete Byskov et al., "Chemical Structure of Sterols that Activate Oocyte Meiosis", Nature, vol. 374, pp. 559–562 (1995).

Christian Grøndahl et al., "Meiosis–Activating Sterol Promotes Resumption of Meiosis in Mouse Oocytes Cultured In Vitro in Contrast To Related Oxysterols", Biology of Reproduction, vol. 58., pp. 1297–1302 (1998).

P. Lonergan et al., "Bovine Blastocyst Production In Vitro after Inhibition of Oocyte Meiotic Resumption for 24 h", Journal of Reproduction and Fertility, vol. 109, pp. 355–365 (1997).

Anne Grete Byskov et al., "Meiosis Activating Sterols (MAS) and Fertility in Mammals and Man", Journal of Experimental Zoology vol. 285., pp. 237–242 (1999).

Hegele–Hartung C., et al., "Oocyte Maturation Can be induced By a Synthetic Meiosis–Activating Sterol (MAS) Leading to an Improvement Of IVF rate in Mice". Human Reproduction, vol. 13, p. 98 (1998).

*Primary Examiner*—Max F. Hindenburg
*Assistant Examiner*—Joseph A. Cadugan
(74) *Attorney, Agent, or Firm*—Reza Green

(57) ABSTRACT

Human infertility can be treated by in vitro methods that actively arrest the human oocyte in prophase of first meiotic division and subsequently actively reverse this meiotic blockage by either adding at least one meiosis-stimulating compound or by culture conditions leading to endogenous formation of meiotic stimulating molecules in the oocyte-cumulus complex.

8 Claims, No Drawings

TREATMENT OF HUMAN INFERTILITY

This application claims the benefit of Provisional application No. 60/241,806 filed Oct. 18, 2000.

The present invention related to a laboratory procedure and a pharmaceutical composition and their use to treat human infertility. More specifically, this invention relates to the treatment of human infertility by in vitro methods that actively arrest the human oocyte in prophase of first meiotic division and subsequently actively reverse this meiotic blockage by either adding at least one meiosis-stimulating compound or by culture conditions leading to endogenous formation of meiosis stimulating molecules in the oocyte-cumulus complex. Briefly, this invention relates to an improved method of in vitro fertilization (hereinafter designated IVF).

BACKGROUND OF THE INVENTION

Meiosis is the unique and ultimate event that occurs to germ cells and on which sexual reproduction is based. Meiosis comprises two meiotic divisions. During the first division, exchange between maternal and paternal genes takes place before the pairs of chromosomes are separated into each of the two daughter cells. These contain only half the number (1n) of chromosomes and 2c DNA. The second meiotic division proceeds without DNA synthesis. This division therefore results in the formation of the haploid germ cells with only 1c DNA.

The meiotic events are similar in male and female germ cells, but the time schedule and the differentiation processes which lead to the formation of ova and spermatozoa differ profoundly. All female germ cells enter the prophase of the first meiotic division early in life, often before birth, but all are arrested as oocytes later in the prophase (dictyate state) until ovulation after puberty. Thus, from early life the female has a stock of oocytes, which is drawn upon until the stock is exhausted. Meiosis in oocytes is not completed until after fertilization, and results in only one ovum and two abortive polar bodies per germ cell. In contrast, only some of the male germ cells enter meiosis from puberty and leave a stem cekk population of germ cells throughout life. Once initiated, meiosis in the male cell proceeds without significant delay and produces 4 spermatozoa.

Little is known about the mechanisms that control meiosis in the male and in the female. In the oocyte, recent studies indicate that follicular purines such as hypoxanthine and adenosine could be responsible for meiotic arrest (Downs, S. M., et al. (1985) in Dev. Biol. 82: 454–458; Eppig, J. J., et al. (1986) in Dev. Biol. 119: 313–321; and Downs, S. M., et al. (1993) in Mol. Reprod. Dev. 35: 82–94). These purine bases were found in follicular fluid in millimolar concentrations (Eppig, J. J., et al. (1985) in Biol. Reprod. 33: 1041–1049). However, the purine base-induced arrest was reversible. This was demonstrated by experiments in which mouse and human oocytes were maintained in meiotic arrest for 24 hours with hypoxanthine followed by a 16–30 hour culture in inhibitor-free medium (Downs, S. M., et al. (1986) in Gamet Res. 15: 305–316; and Cha, K. Y., et al. (1992) in Reprod. Fertil. Dev. 4: 695–701). Nearly 100% of the arrested mouse oocytes resumed maturation and, furthermore, the mature oocytes were successfully fertilized and demonstrated complete pre- and post-implantation development. These data collectively support the idea that purines such as hypoxanthine and adenosine are physiologically important in the mechanisms controlling meiotic arrest in vivo.

Cyclic adenosine 5'-monophosphate (hereinafter designated cAMP) plays a pivotal role as a second messenger in the signal transduction pathway during meiosis in the oocyte. cAMP is generated by the action of adenylate cyclase (hereinafter designated AC). cAMP is degraded by the family of phosphodiesterase enzymes (hereinafter designated PDE), which produces inactive second messenger products. Hypoxanthine (hereinafter designated Hx) is an inhibitor of cAMP PDE (Eppig, J. J., et al. (1985) in Biol. Reprod. 33: 1041–1049). As such, Hx can prevent the hydrolysis of oocyte cAMP and thereby maintain elevated levels of cAMP in the oocyte. In addition to hypoxanthine, agents acting upstream or downstream of cAMP are able to increase cAMP levels. By this mechanism, activation of AC with forskolin, inhibition of PDE with the nonselective 3-isobutyl-1-methylxanthine (hereinafter designated IBMX), or inhibition of the oocyte-specific isoform PDE3 with a specific PDE3-inhibitor, for example milrinone, leads to meiotic arrest by maintaining elevated levels of c-AMP within the oocytes (Downs, S. M., and Hunzicker-Dunn, M., (1995) in Dev Biol 172: 72–85; and Tsafiri, A., et al. (1996) in Dev Biol 178: 393–402).

A PDE3 specific inhibitor has been described as a contraceptive agent (WO98/10765).

The presence of a diffusible meiosis regulating substance was first described (Byskov, A. G., et al. (1976) in Dev. Biol. 52: 193–200) in foetal mouse gonads. A meiosis activating substance (MAS) was secreted in the foetal mouse ovaries in which meiosis was ongoing, and a meiosis preventing substance (hereinafter designated MPS) was released from morphologically differentiated testes containing resting, non-meiotic germ cells. It was, therefore, suggested that the relative concentrations of MAS and MPS regulated theinitiation, arrest, and resumption of meiosis in male and female germ cells (Byskov, A. G., and Hoyer, P. E., (1994) in The Physiology of Reproduction, Knobil, E., and Neill, J. D., (Editors), Raven Press, New York, pp. 487–540). A recent article (Byskov, A. G., et al. (1995) in Nature 374: 559–562) describes the isolation of certain sterols from preovulatory ovarian follicular fluid, defined as FF-MAS, and bull testicular testis, defined as T-MAS, that activate oocyte meiosis. This was confirmed recently (Grøndahl et al. (1998) in Biol. Reprod. 1998; 58:1297–1302) by showing that de novo synthesized FF-MAS is capable of mediating resumption of meiosis in mice oocytes.

Since the first IVF baby was delivered in 1978, this procedure has resulted in thousands of pregnancies and opened a vast new frontier of research and treatment for infertile couples. Still, there is a significant need for improved infertility treatment modalities today. It is presumed that about one out of seven couples experience problems with sub-fertility or infertility.

IVF of human oocytes has become commonly used for the treatment of female and male sub-fertility. The standard IVF treatment includes a long phase of hormone stimulation of the female patient, for example 30 days, which is initiated by suppressing the patient+s own follicle stimulating hormone (hereinafter designated FSH) and luteinizing hormone (hereinafter designated LH) by gonadotropin releasing hormone (hereinafter designated GnRH), and this is followed by injections of exogenous gonadotropins, for example FSH and/or LH, in order to ensure development of multiple preovulatory follicles and aspiration of multiple in vivo matured oocytes immediately before ovulation. The aspirated oocyte is subsequently fertilized in vitro and cultured, typically for three days, before transfer back into the uterus at the 4–8 cell stage. Continuous efforts have been made to optimise and simplify this procedure. Nevertheless, the overall pregnancy rate cannot be increased significantly over about 20% with the current treatment modalities. In a large European survey of IVF patients, it was found that 7.2 oocytes out of 11.5 aspirated oocytes per patient had undergone resumption of meiosis immediately before fertilization, only 4.3 oocytes were fertilized and only 2.2 oocytes reached the 8-cell embryo stage after fertilization and in vitro culture (ESHRE, Edinburgh, 1997).

Due to the very unpredictable quality of the state of the art embryos today, more than one embryo has to be transferred just to give a reasonable chance of success. Therefore, it is common to transfer 2–3 embryos (up to 5 embryos in some countries), which carries the very large side effect of multiple pregnancies with great discomfort and risk to both patient and children. Moreover, it has been estimated that the increased health care expense due to multiple birth (twins, triplets etc.) exceedsthe entire cost of IVF.

Hence, there are several disadvantages associated with current treatments, the four most notable being:
1. the risk of ovarian hyperstimulation caused by injecting gonadotropins, a potentially fatal condition that requires hospitalisation,
2. multiple pregnancies (50–1.000 times the normal frequency of twins and triplets, respectively),
3. the existence of considerable patient subpopulations that do not tolerate the current method due to, for example polycystic ovarian syndromeor diabetes, and
4. a potential long-term cancer risk.

Furthermore, weight gain, bloating, nausea, vomiting, labile mood and other patient discomforts, together with the reluctance of patients to self-inject, are reported as disadvantages.

At present, in vitro maturation of human oocytes has proven highly unsuccessful, despite substantial interest and clinical efforts.

SUMMARY OF THE INVENTION

Recently, we have discovered that spontaneous maturation and MAS-induced maturation make use of different signalling mechanisms. Spontaneous maturation does not make use of a cholera toxin sensitive signalling mechanism, in contrast to MAS-induced maturation. This implies that different receptors, i.e., G-protein coupled receptors, are involved in the two signalling mechanisms. Furthermore, we have observed that the kinetics of spontaneous and FF-MAS induced oocyte maturation are completely different. The naked mouse oocyte matures spontaneously within 4 hours, whereas the meiotically arrested mouse oocyte (arrested by either massive cumulus cell enclosure or by various purines) upon FF-MAS or FSH activation matures over 16–20 hours.

We have also observed that FF-MAS in cumulus enclosed human oocytes improves not only nuclear but cytoplasmic maturation (Grøndahl et al., 1999 Alpha abstract, Copenhagen). Although the use of FF-MAS improves the rate of fertility compared to the currently applied methods, it is still desirable to increase this rate even further.

The present invention relates to improving infertility treatment by avoiding spontaneous maturation of oocytes in vitro and promoting an active induction of maturation.

This is accomplished by methods by which oocyte maturation is blocked. Subsequently, this meiosis block is actively reversed.

DETAILED DESCRIPTION OF THE INVENTION

One of the processes invented and claimed herein is performed on an oocyte removed or taken from a woman, for example, from a female, human patient or from a female, human donor. The process comprises the following steps:
1) subjecting an oocyte removed from a woman to conditions causing oocyte arrest (hereinafter designated the step of arresting),
2) subjecting the oocyte to conditions wherein the arrested state is reversed (hereinafter designated the step of reversing), and
3) fertilizing the oocyte (hereinafter designated the step of fertilization), with the proviso that from the moment when the oocyte is removed from the patient or donor and in the following 16 hours, preferably the following 8 hours, more preferred the following 4 hours, even more preferred the following 2 hours, and even more preferred the following hour, no or substantially no spontaneous maturation takes place.

Alternatively, the proviso in the above process is worded as follows: "with the proviso that from the moment when the oocyte is removed from the patient or donor and in the following 16 hours, preferably the following 8 hours, most preferred the following 4 hours, no or substantially no germinal vesicle breakdown appears before resumption of meiosis is actively induced."

Before performing the above process, at least one oocyte is removed from a woman, e.g., a female patient or donor. This removal may be performed in the known manner, for example as described by Itskovitz-Eldor & Thaler (In Reproductive, Endocrinology, Surgery and Technology Chapter 107 pp1991–2030, Editors: Adashi, Rock and Rosenwaks, 1995, Lippencott-Raven publishers). Usually, 5–15 oocytes are removed. All of the removed oocytes, or only some of them, may be subjected to the process of this invention.

The oocytes used for this invention should have completed the growth phase in which they acquire full competence to resume meiotic maturation. The completion of said growth phase occurs during the follicular dynamics. Preferably, the follicles have a diameter of at least about 5 mm and, preferably, the follicles have a diameter of not more than about 10 mm.

The female patient is a woman for whom it has been decided to perform IVF. Alternatively, an egg donor may be used.

Meiotic Arrest

After removal of an oocyte from the meiosis inhibitory milieu, i.e., a patient's or donor's follicle, the oocyte is subjected to conditions causing the oocyte to maintain meiotic arrest or, in other words, is subjected to conditions by which the spontaneous maturation of the oocyte is avoided, i.e., the step of arresting. The condition causing the oocyte to arrest can be obtained in any known way. For example, this meiosis arresting condition may be obtained by blocking oocyte maturation with whatever method, for example, culturing cumulus enclosed oocytes alone or together in co-culture with cumulus cells, theca cells, granulosa cells, somatic cells, or in conditioned media with concentration of autocrine and paracrine factors that the above-listed cells may produce in culture, or by adding any chemical meiosis inhibitor to the medium, such as, for example, purines.

The meiotic status of the oocytes can be observed and followed by monitoring the progression of the nuclear maturation, for example, the presence or absence of an intact nuclear membrane. The immature (meiotically arrested) oocytes display a spherical germinal vesicle (hereinafter designated GV) which will undergo membrane breakdown upon resumption of meiosis. Germinal vesicle breakdown (hereinafter designated GVB) can be recognised by light microscopic investigations of the living oocytes using an inverted microscope with Nomarksi or Hoffamann optics.

Preferably, the period of time in which the oocyte is subject to conditions maintaining meiotic arrest is between about 1 hour and about 48 hours, preferably between about 8 hours and about 22 hours.

While the oocyte has been subjected to conditions causing meiotic inhibition (also designated oocyte arrest), it may be desirable to culture the oocyte for a period of time. Conveniently, the period of time for this cultivation is in the range from about 1 hour to about 44 hours, preferably in the range from about 4 hours to about 36 hours. Preferably, the oocyte is cultured in a medium such as TCM-199 or a simple Earle's balanced salt solution, see Bavister or Gardner. The storage is preferably performed at a temperature in the range from about 36° C. and about 39° C., preferably in the range from about 37° C and about 37.5° C.

Reversal of Meiotic Arrest

After the oocyte is subjected to conditions causing meiotic arrest, the oocyte is subjected to conditions under which the arrested state is reversed or, in other words, the meiosis block is reversed. Hence, at the step at which the arrested step is reversed, the component causing the arrest in the previous step may still be present. Preferably, the arrested state is reversed by the addition of one or more meiosis activating substances (hereinafter designated MAS) or by a media composition that make the cultured cells produce or secrete substances mediating a resumption of meiosis.

It is known from WO 96/00235 that certain sterol derivatives can be used for regulating meiosis. An example of such a sterol is 4,4-dimethyl-5α-cholesta-8,14,24-triene-3β-ol (hereinafter designated FF-MAS).

Herein, the term MAS designates compounds which mediate the meiosis of oocytes. More specifically, MAS is a compound, which in the test described in Example 1 below has a percentage germinal vesicle breakdown (hereinafter designated GVB) that is significantly higher than the control. A preferred MAS is a compound having a percentage GVB of at least 50%, preferably at least 80%.

Examples of MASs are mentioned in WO 96/00235, 96/27658, 97/00884, 98/28323, 98/54965 and 98/55498, more specifically in claim 1 thereof.

In WO 95/000265, some potential MASs were tested on immature female mice. Forty-eight hours before the test animals were killed by cervical dislocation, they were given a single injection of human menopausal gonadotropin containing 20 IU FSH and 20 IU LH. The ovaries were removed, placed in a hypoxanthine medium and freed of extraneous tissue. Then, the oocytes were punctured out of the follicles, freed from cumulus cells and cultured in a medium containing a meiosis-regulating derivative.

Preferably, the period of time in which the oocyte is subjected to conditions under which the arrested state is reversed is from about 1 hour to about 48 hours, preferably from about 4 hours to about 36 hours.

Preferably, the period of time from which the oocyte is subjected to conditions causing them to maintain meiotic arrested and until the oocyte is subjected to conditions under which the arrested state is reversed is from about 0 hours to about 24 hours, preferably from about 1 hour to about 4 hours.

Fertilization

After the oocyte is subjected to conditions under which the arrested state is reversed, the oocyte is fertilized. The fertilization is performed in a manner known per se, either by standard in vitro fertilization (IVF) or by intracytoplasmic sperm injection (ICSI), for example, as described in an overview article by Davis & Rosenwaks (in Reproductive, Endocrinology, Surgery and Technology Chapter 124, pp. 2319–2334, Editors: Adashi, Rock and Rosenwaks, 1995, Lippencott-Raven publishers).

After the oocyte is fertilized, the zygote is allowed to develop a few days in culture and is subsequently transferred to the uterus of the patient or cryopreserved. Preferably, this is done in a manner known per se.

Most of the steps in the above treatment are performed in a known manner and the remaining steps are performed in a manner known per se.

In a preferred embodiment of this invention, the process comprises the following steps:

(a) removing an oocyte from a female patient or donor, (b) subjecting the oocyte to conditions causing meiotic arrest, (c) subjecting the oocyte to conditions wherein the arrested state is reversed, (d) fertilizing the oocyte, and allowing the zygote to develop before transfer or cryopreservation.

The present invention is further illustrated by the following examples, which, however, are not to be construed as limiting the scope of protection. The features disclosed in the foregoing description and in the following examples may, in any combination thereof, be material for realising the invention in diverse forms thereof.

EXAMPLE 1

Method used for electing an MAS

Oocytes were obtained from immature female mice (C57BL/6J×DBA/2J F1, Bomholtgaard, Denmark) weighing 13–16 grams, that were kept under controlled temperature (20–22° C.),light (lights on 06.00–18.00), and relative humidity (50–70%). The mice received an intra-peritoneal injection of 0.2 ml gonadotropin (Gonal-F, Serono) containing 20 IU FSH, and 48 hours later the animals were killed by cervical dislocation. The ovaries were dissected out and the oocytes were isolated in Hx-medium (see below) under a stereomicroscope by manual rupture of the follicles using a pair of 27 gauge needles. Spherical oocytes displaying an intact germinal vesicle (hereinafter designated GV) were divided in cumulus enclosed oocytes (hereinafter designated CEO) and naked oocytes (hereinafter designated NO) and placed in α-minimum essential medium (α-MEM without ribonucleosides, Gibco BRL, Cat. No. 22561) supplemented with 3 mg/ml bovine serum albumin (BSA, Sigma Cat. No. A-7030), 5 mg/ml human serum albumin (HSA, State Serum Institute, Denmark), 0.23 mM pyruvate (Sigma, Cat. No S-8636), 2 mM glutamine (Flow Cat. No. 16–801), 100 IU/ml penicillin and 100 μg/ml streptomycin (Flow, Cat No. 16–700). This medium was supplemented with 3 mM hypoxanthine (Sigma Cat. No. H-9377) and designated Hx-medium.

The oocytes were rinsed three times in Hx-medium and oocytes of uniform size were divided into groups of CEO and NO. CEO and NO were cultured in 4-well multidishes (Nunclon, Denmark) in which each well contained 0.4 ml of Hx-medium and the compound to be tested in a concentration of 10 μM. One control well (i.e., 35–45 oocytes cultured in identical medium with no addition of test compound) was always cultured simultaneously with 3 test wells (35–45 oocytes per well supplemented with test compound).

The oocytes were cultured in a humidified atmosphere of 5% $CO_2$ in air for 24 hours at 37° C. By the end of the culture period, the number of oocytes with GV, GVB and polar bodies (hereinafter designated PB), respectively, were counted using a stereomicroscope (Wildt, Leica MZ 12). The percentage of GVB, defined as percentage of oocytes undergoing GVB per total number of oocytes in that well, was calculated as:

% GVB=((number of GVB+number of PB)/total number of oocytes)×100.

EXAMPLE 2

Method used to isolate and culture human oocytes

The female patient is a woman for whom it has been decided to perform IVF or ICSI. The patient will, after a gynaecological examination, be subjected to the following hormone pre-treatment: Down regulation with gonadotropin releasing hormones, stimulation of follicular growth with exogenous recombinant or urinary based human FSH and final oocyte maturation induced by human chorion gonadotropin (hereinafter designated hCG) displaying LH activity. The oocytes are aspirated under sedation via ultrasound guided transvaginal follicle aspiration of middle to large size follicles (12–20 mm follicles in diameter).

After the removal of an oocyte from the meiosis inhibitory milieu of a patient's follicle, the oocyte is subjected to conditions causing the oocyte to maintain meiotic arrest or, in other words, which avoids the spontaneous maturation of the oocyte. This meiosis arresting condition is obtained by blocking the oocyte maturation by culturing cumulus enclosed oocytes together in co-culture with cumulus cells/ granulosa cells or by adding the physiological PDE inhibitor hypoxanthine to the medium, for example in a concentration of 3 mM.

After 1 hour in medium TCM-199 including granulosa cells and hypoxanthine to ensure meiotic arrest, 20 μM FF-MAS was added to the medium, and the culture was continued for 24 hours at a temperature of about 37.4° C. to overcome the meiotic arrest.

EXAMPLE 3

Method used to isolate and culture immature human oocytes

The female patient is a woman for whom it has been decided to perform IVF or ICSI. The patient will, after a gynaecological examination, be subjected to the following hormone pre-treatment: On day 6 in the cycle (day 0 is the first day of menses), a short stimulation of small follicles is induced by 3 days' injection of 225 IE exogenous recombinant or urinary based human FSH. The immature oocytes are aspirated under sedation via ultrasound-guided transvaginal follicle aspiration of small to middle size follicles 6–12 mm in diameter. After the removal of an oocyte from the meiosis inhibitory milieu, i.e., a patient's follicle, the oocyte is subjected to conditions causing the oocyte to maintain meiotic arrest or, in other words, conditions that avoid spontaneous maturation of the oocyte. This meiosis arresting condition is obtained by blocking the oocyte maturation by culturing cumulus enclosed oocytes together in co-culture with cumulus cells/ granulosa cells or by adding the physiological PDE inhibitor hypoxanthine to the medium for example in a concentration of 3 mM.

After 1 hour in medium TCM-199 including granulosa cells and hypoxanthine to ensure meiotic arrest, 20 μM FF-MAS was added to the medium, and the culture continued for 36 hours to overcome the meiotic arrest.

EXAMPLE 4

Aim: to optimize the culture conditions for mammalian oocytes by arresting the spontaneous maturation for 4 hours before initiating oocyte maturation by the means of adding a adequate concentration of FF-MAS.

Óocytes were obtained from immature (21–24 day old) female mice (C57Bl/6J×DBA/2J F1-hybrids, M&B, Denmark) weighing 13–16 grams, which were kept under controlled lighting and temperature. The mice received an intra-peritoneal injection of 0.2 ml gonadotropin (Gonal-F, Serono) containing 20 IU FSH and 48 hours later the animals were killed by cervical dislocation. The ovaries were dissected out and the oocytes were isolated in Hx-medium (see below) under a stereomicroscope by manual rupture of the follicles using a pair of 27 gauge needles. Spherical oocytes displaying an intact germinal vesicle (GV) were selected and placed in α-minimum essential medium (α-MEM without ribonucleosides, Gibco BRL, Cat. No. 22561) supplemented with 3 mM hypoxanthine (Sigma Cat. No. H-9377), 8 mg/ml Human Serum Albumin (HSA, State Serum Institute, Denmark), 0.23 mM pyruvate (Sigma, Cat. No. S-8636), 2 mM glutamine (Flow Cat. No. 16-801), 100 IU/ml penicillin and 100 μg/ml streptomycin (Flow, Cat. No. 16-700). This medium was designated Hx-medium. The exact same medium without Hx was designated Hx-free medium Thus oocytes were cultured in 4-well multidishes (Nunclon, Denmark) in which each well contained 0.4 ml of Hx-medium or medium without Hx (to allow for spontaneous maturation) and 35–45 oocytes.

Different treatment groups:
1. Controls: No inhibition, No FF-MAS
2. MAS: No inhibition and 10 μM FF-MAS
3. Inhibition and then spontaneous maturation: Hx-medium for 4 hours then transfer to Hx-free medium
4. Inhibition and FF-MAS induction: Hx-medium for 4 hours and addition of FF-MAS to Hx-medium
5. Inhibition and removal of inhibition and then subsequently FF-MAS induction: Hx-medium for 4 hours, rinse, transfer to Hx-free medium and addition of FF-MAS.

In vitro fertilization following 16–20 hours maturation.

Endpoints: Fertilization rate and in vitro embryo development.

Results

| Treatment | Fertilization Rate | Embryo development Rate (8-cell rate at 72 hours) |
| --- | --- | --- |
| Treatment No 1 | <50% | <10% |
| Treatment No 2 | <50% | <10% |
| Treatment No 3 | <50% | <10% |
| Treatment No 4 | 75%* | 30%* |
| Treatment No 5 | <50% | <10% |

One out of 5 treatments were superior to the others in terms of oocyte quality evaluated as fertilization rate and embryonic developmental capacity.

The 4$^{th}$ treatment modality, i.e., inhibition and FF-MAS induction was significantly superior to the other treatment alternatives.

What is claimed is:

1. A process for in vitro fertilization, said method comprising:
    a) subjecting an oocyte removed from a woman to conditions under which the oocyte is meiotically arrested for at least about 1 hour, b) subjecting the arrested oocyte to conditions causing a release of said meiotic arrest, wherein said conditions comprise contacting the arrested oocyte with a meoisis activating substance (MAS), and c) fertilizing the oocyte.

2. A process as defined in claim 1, wherein substantially no germinal vesicle breakdown appears prior to said release of said meiotic arrest.

3. A process as defined in claim 1, further comprising: (d) subjecting the fertilized oocyte to conditions under which the oocyte develops into an embryo.

4. A process as defined in claim 1, wherein the conditions causing a release of said meiotic arrest comprise endogenous formation of meiotic stimulating molecules in the oocyte-cumulus complex.

5. A process as defined in claim 1, wherein, in step (a), said oocytes are meiotically arrested for at least about 2 hours.

6. A process as defined in claim 5, wherein, in step (a), said oocytes are meiotically arrested for at least about 4 hours.

7. A process as defined in claim 6, wherein, in step (a), said oocytes are meiotically arrested for at least about 8 hours.

8. A process as defined in claim 7, wherein, in step (a), said oocytes are meiotically arrested for at least about 16 hours.

* * * * *